(12) United States Patent
Baba et al.

(10) Patent No.: US 10,040,742 B2
(45) Date of Patent: Aug. 7, 2018

(54) METHOD OF PRODUCING ALIPHATIC ALDEHYDE COMPOUND HAVING TERMINAL CONJUGATED DIENE STRUCTURE AND INTERMEDIATE THEREFOR

(71) Applicant: SHIN-ETSU CHEMICAL CO., LTD., Chiyoda-ku, Tokyo (JP)

(72) Inventors: Akihiro Baba, Joetsu (JP); Yuki Miyake, Joetsu (JP); Takeshi Kinsho, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 15/473,150

(22) Filed: Mar. 29, 2017

(65) Prior Publication Data

US 2017/0297987 A1 Oct. 19, 2017

(30) Foreign Application Priority Data

Apr. 18, 2016 (JP) .................. 2016-083120

(51) Int. Cl.
| | | |
|---|---|---|
| C07C 43/00 | (2006.01) | |
| C07C 41/48 | (2006.01) | |
| C07C 45/42 | (2006.01) | |
| C07C 43/315 | (2006.01) | |
| C07C 41/20 | (2006.01) | |
| C07C 41/30 | (2006.01) | |
| C07C 43/178 | (2006.01) | |
| C07C 45/81 | (2006.01) | |

(Continued)

(52) U.S. Cl.
CPC ............ *C07C 43/315* (2013.01); *C07C 41/20* (2013.01); *C07C 41/30* (2013.01); *C07C 41/48* (2013.01); *C07C 43/178* (2013.01); *C07C 45/42* (2013.01); *C07C 45/81* (2013.01); *C07C 45/82* (2013.01); *C07C 47/21* (2013.01)

(58) Field of Classification Search
CPC ....... C07C 43/315; C07C 41/48; C07C 45/42; C07C 45/515
See application file for complete search history.

(56) References Cited

U.S. PATENT DOCUMENTS

2010/0113837 A1 5/2010 Bedoukian et al.

OTHER PUBLICATIONS

Eynard et al. Synthesis of Methyl (5Z, 8Z, 11Z, 14Z, 17Z)- and (5Z, 8Z, 11Z, 14Z, 17E)-[18—14C] Eicosapentaenoate. Journal of Labelled Compounds and Radiopharmaceuticals, XLI, 1998, 411-421.*

European Patent Office, European Search Report based on 17164722.5-1451, dated Jun. 26, 2017.
McLean, J.A., et al. "Behavior and Survival of Western Spruce Budworm, Choristoneura occidentalis Freeman, Exposed to an w-Fluorinated Pherome Analogue", Department of Forest Sciences, Department of Chemistry, University of British Columbia, Journal of Chemical Ecology, vol. 15, No. 1, 1989, pp. 91-103.

(Continued)

*Primary Examiner* — Sikarl A Witherspoon
(74) *Attorney, Agent, or Firm* — Williams Mullen; F. Michael Sajovec

(57) ABSTRACT

Provided are a method for producing a terminal conjugated dienal compound without an oxidation reaction and a terminal hydroxyacetal compound useful as an intermediate in the method. More specifically, provided are a method for producing an (E)-dienal compound comprising the steps of: a metalation reaction of an alkynal acetal compound (1) to obtain an organic metal compound (2), an addition reaction of (2) to ethylene oxide to obtain a hydroxyalkynal acetal compound (3), a reduction reaction of (3) to obtain an (E)-hydroxyalkenal acetal compound (4), a functional group conversion reaction of (4) to obtain an (E)-alkenal acetal compound (5) having a leaving group X, an elimination reaction of (5) to obtain an (E)-dienal acetal compound (6), and a hydrolysis reaction of (6) to obtain the (E)-dienal compound (7); and others.

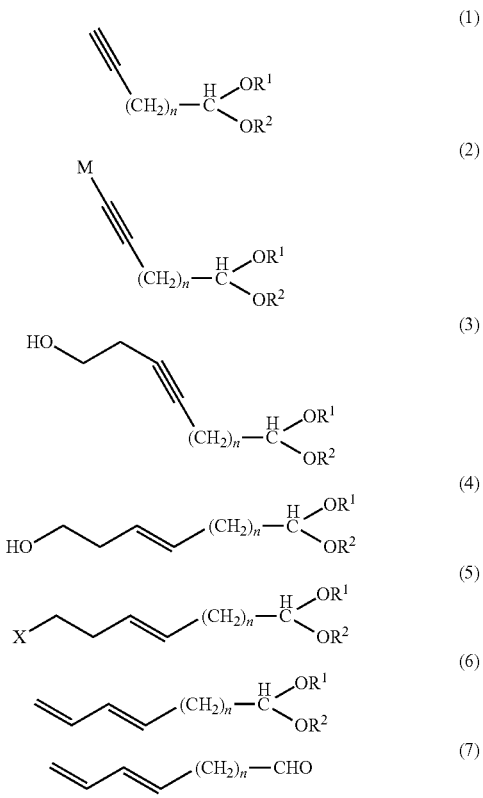

7 Claims, No Drawings

(51) Int. Cl.
*C07C 45/82* (2006.01)
*C07C 47/21* (2006.01)

(56) References Cited

OTHER PUBLICATIONS

Legrand, Sacha, et al. "Syntheseis and Field Tests of Sex Pheromone Components of the Leafroller Argyrotaenia sphaleropa", Department of Chemistry and Biomedical Sciences, University of Kalmar, 59c, pp. 708-712, 2005, Kalmar, Sweden.

* cited by examiner

METHOD OF PRODUCING ALIPHATIC ALDEHYDE COMPOUND HAVING TERMINAL CONJUGATED DIENE STRUCTURE AND INTERMEDIATE THEREFOR

CROSS-REFERENCE TO RELATED APPLICATION

This application claims priority to Japanese Patent Application No. 2016-083120 filed Apr. 18, 2016; the entire disclosure of the application is incorporated herein by reference.

BACKGROUND OF THE INVENTION

1. Field of the Invention

The present invention relates to a method of producing an aliphatic aldehyde compound having a terminal conjugated diene structure, which is, for example, a sex pheromone of insects; and a synthetic intermediate to be used for the method.

2. Description of the Related Art

A sex pheromone of insects is generally a bioactive substance being released by female individuals and having a function of attracting male individuals, and exhibits high attracting activity even in a small amount. The sex pheromone has been used widely as a means for predicting the emergence of insects or finding geological spread thereof (invasion in specific areas) or as a means for pest control. As the means for pest control, a control method called "mass trapping", "lure & kill or attract & kill", "lure & infect or attract & infect" or "mating disruption" has been widely in practice. In use of the sex pheromone for basic research and further for applied research, economical production of a required amount of sex pheromone is necessary.

The blackheaded budworm is a defoliator spreading in the United States of America and seriously damaging a forest land. As the sex pheromone of the blackheaded budworm, (E)-11,13-tetradecadienal is known.

There has been reported a method for producing the (E)-11,13-tetradecadienal comprising the steps of: converting 9-chlorononanal diethyl acetal into a Grignard reagent, reacting the Grignard reagent with 1,4-pentadien-3-yl isobutyrate, and then hydrolyzing the resulting acetal (JP 2012-507520T, which is a Japanese phase publication of WO 2010/051028).

The South American tortricid moth is distributed in South American countries such as Uruguay and Brazil. It damages various crops such as deciduous fruit trees and grapes so that it is an economically important insect pest.

According to the report by Legrand et al., it is found in the trap test of South American tortricid moth that a 10:1 mixture of (Z)-11,13-tetradecadienal and (Z)-11,13-tetradecadienyl acetate is a combination having the highest attracting effect (Z. Naturforsch., 59C, 709-712 (2004)). In this article, they also report a synthesis of the (Z)-11,13-tetradecadienyl acetate involving acetylation of 11-bromo-1-undecanol, conversion into a phosphonium salt, and a Wittig reaction between acrolein and a phosphorus ylide prepared from the phosphonium salt to obtain the (Z)-11,13-tetradecadienyl acetate; and a synthesis of (Z)-11,13-tetradecadienal through hydrolysis and oxidation of the (Z)-11,13-tetradecadienyl acetate.

SUMMARY OF THE INVENTION

In the method of JP 2012-507520T, however, the overall yield of 11,13-tetradecadienal from 9-chlorononanal diethyl acetal is as low as 24.3%. In addition, although this method comprises simultaneous formation of the main chain and a terminal conjugated diene, it is considered to be difficult to obtain a high-purity terminal diene because the terminal conjugated diene is not stable so that conversion into an organic metal compound such as a Grignard reagent may result in geometric isomerization of a double bond. In fact, the 11,13-tetradecadienal obtained by the method has an E isomer and a Z isomer at a ratio of 76:24 and thus, the purity of the E isomer is not so high.

In the synthesis of Z. Naturforsch, 59C, 709-712 (2004), the main chain and a terminal conjugated diene are formed simultaneously through a Wittig reaction. However, the isolation yield after purification is as low as 22%, acrolein to be used as a raw material is not easily industrially available, and the reaction temperature of −78° C. is difficult to be carried out industrially. Further, this synthesis is accompanied with the problems such as removal or disposal of a large amount of triphenylphosphine oxide produced as a by-product. It is therefore industrially difficult to make use of the Wittig reaction for the synthesis of a terminal dienal compound. In this article, the aldehyde is produced through the oxidation of an alcohol, but pyridinium dichromate (PDC) used as an oxidizing agent in this reaction produces a harmful chromium waste, making it difficult to industrially perform this method. Further, it is difficult to regard this synthesis as an industrial synthesis because chromatography is used for isolation or purification of an intermediate in each step and an overall yield of (Z)-11,13-tetradecadienal from 11-bromo-1-undecanol is only 4.5%.

Thus, it is considered to be industrially very difficult to produce a sufficient amount of (E)-11,13-tetradecadienal and (Z)-11,13-tetradecadienal in the conventional production methods from the standpoint of their yields, isolation or purification of intermediates and the intended products, and others.

Since an isomer purity and the yield are considered to be possibly low in the method for producing a terminal conjugated dienal through a homologation reaction accompanied with formation of a terminal conjugated diene or through a homologation reaction after formation of a terminal conjugated diene, the inventors have thought that formation of a terminal conjugated diene after formation of a necessary carbon skeleton can result in the production of a terminal conjugated dienal compound with a high isomer purity and in good yield. The inventors have also thought that use of an acetal-containing compound as an aldehyde precursor can result in synthesis of a corresponding aldehyde without an oxidation reaction.

In other words, the inventors have thought that if a compound containing an alkyne part and an acetal part can be synthesized, the alkyne part can be selectively reduced to an (E)- or (Z)-alkene, and then subjected to formation of a terminal conjugated diene and hydrolysis to obtain the E isomer or Z isomer of a terminal conjugated dienal compound with high purity.

With the foregoing in view, the invention has been made. An object of the invention is to provide a method for producing a terminal conjugated dienal compound with a good purity and in good yield without an oxidation reaction so as to supply a sufficient amount of product necessary for biological or agricultural active tests, practical applications or utilizations and others; and a terminal hydroxyacetal compound which is an intermediate useful for the production of the terminal conjugated dienal compound.

In one aspect of the invention, there is provided a method of producing an (E)-dienal compound, comprising the steps of:

metalizing a terminal alkyne of an alkynal acetal compound represented by formula (1):

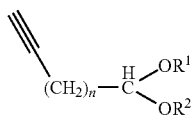
(1)

wherein n is an integer of from 2 to 11, and $R^1$ and $R^2$ each independently represents a monovalent hydrocarbon group having from 1 to 10 carbon atoms, or $R^1$ and $R^2$ are coupled together to form a divalent hydrocarbon group having from 2 to 10 carbon atoms, through a metalation reaction of the alkynal acetal compound to obtain an organic metal compound represented by formula (2):

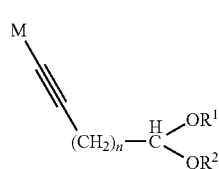
(2)

wherein M represents a cationic moiety;

reacting the organic metal compound with ethylene oxide through an addition reaction to obtain a hydroxyalkynal acetal compound represented by formula (3):

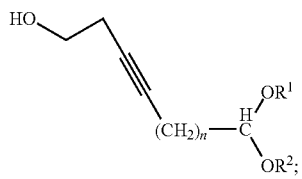
(3)

reducing the hydroxyalkynal acetal compound through a reduction reaction of converting a triple bond of the hydroxyalkynal acetal compound into an (E)-double bond to obtain an (E)-hydroxyalkenal acetal compound represented by formula (4):

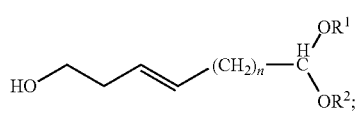
(4)

converting a hydroxyl group of the (E)-hydroxyalkenal acetal compound into a leaving group X through a functional group conversion reaction of the (E)-hydroxyalkenal acetal compound to obtain an (E)-alkenal acetal compound having the leaving group X represented by formula (5):

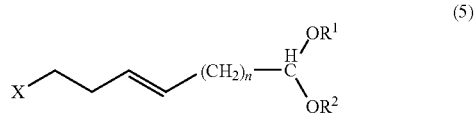
(5)

wherein X represents a leaving group;

eliminating HX from the (E)-alkenal acetal compound having the leaving group X through an elimination reaction of the (E)-alkenal acetal compound to obtain an (E)-dienal acetal compound represented by formula (6):

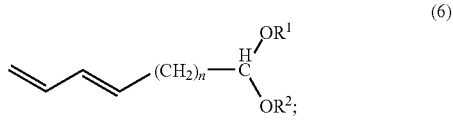
(6)

and hydrolyzing the (E)-dienal acetal compound through a hydrolysis reaction of converting an acetal of the (E)-dienal acetal compound into an aldehyde to obtain the (E)-dienal compound represented by formula (7):

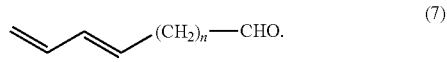
(7)

In another aspect of the invention, there is provided a method of producing a (Z)-dienal compound, comprising the steps of:

metalizing a terminal alkyne of an alkynal acetal compound represented by the formula (1):

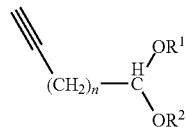
(1)

wherein n is an integer of from 2 to 11, and $R^1$ and $R^2$ each independently represents a monovalent hydrocarbon group having from 1 to 10 carbon atoms, or $R^1$ and $R^2$ are coupled together to form a divalent hydrocarbon group having from 2 to 10 carbon atoms, through a metalation reaction of the alkynal acetal compound to obtain an organic metal compound represented by formula (2):

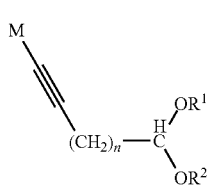
(2)

wherein M represents a cationic moiety;

reacting the organic metal compound with ethylene oxide through an addition reaction to obtain a hydroxyalkynal acetal compound represented by formula (3):

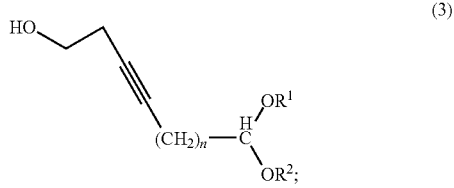
(3)

reducing the hydroxyalkynal acetal compound through a reduction reaction of converting a triple bond of the hydroxyalkynal acetal compound into a (Z)-double bond to obtain a (Z)-hydroxyalkenal acetal compound represented by formula (8):

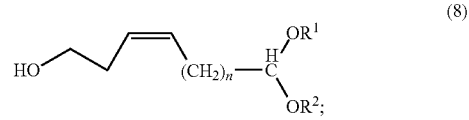
(8)

converting a hydroxyl group of the (Z)-hydroxyalkenal acetal compound into a leaving group X through a functional group conversion reaction of the (Z)-hydroxyalkenal acetal compound to obtain a (Z)-alkenal acetal compound having the leaving group X represented by formula (9):

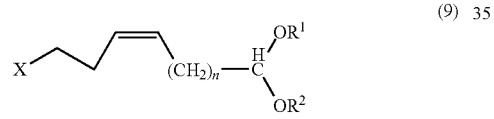
(9)

wherein X represents a leaving group;

eliminating HX from the (Z)-alkenal acetal compound having the leaving group X through an elimination reaction of the (Z)-alkenal acetal compound to obtain a (Z)-dienal acetal compound represented by formula (10):

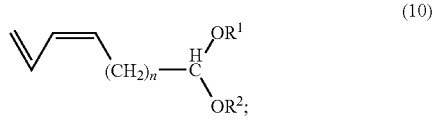
(10)

and hydrolyzing the (Z)-dienal acetal compound through a hydrolysis reaction of converting an acetal of the (Z)-dienal acetal compound into an aldehyde to obtain the (Z)-dienal compound represented by formula (11):

(11)

In a further aspect of the invention, there is also provided a hydroxyalkynal acetal compound represented by formula (3):

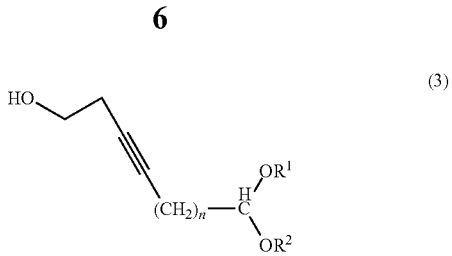
(3)

wherein n is an integer of from 2 to 11, and $R^1$ and $R^2$ each independently represents a monovalent hydrocarbon group having from 1 to 10 carbon atoms, or $R^1$ and $R^2$ are coupled together to form a divalent hydrocarbon group having from 2 to 10 carbon atoms.

In a still further aspect of the invention, there is also provided an (E)-hydroxyalkenal acetal compound represented by formula (4):

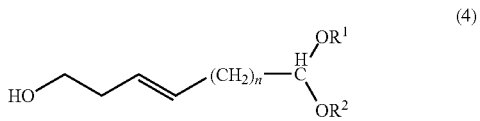
(4)

wherein n is an integer of from 2 to 11, and $R^1$ and $R^2$ each independently represents a monovalent hydrocarbon group having from 1 to 10 carbon atoms, or $R^1$ and $R^2$ are coupled together to form a divalent hydrocarbon group having from 2 to 10 carbon atoms.

In a still further aspect of the invention, there is also provided a (Z)-hydroxyalkenal acetal compound represented by formula (8m):

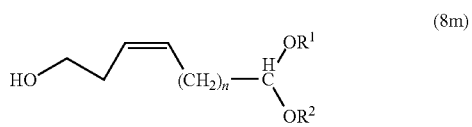
(8m)

wherein m is an integer of from 5 to 11, and $R^1$ and $R^2$ each independently represents a monovalent hydrocarbon group having from 1 to 10 carbon atoms, or $R^1$ and $R^2$ are coupled together to form a divalent hydrocarbon group having from 2 to 10 carbon atoms.

According to the invention, the E isomer or the Z isomer of a terminal conjugated dienal compound can be produced by formation of a hydroxyalkynal acetal compound (3) containing an alkyne part and an acetal part, selective reduction of the alkyne part into an (E)-alkene or (Z)-alkene part, formation of a terminal conjugated diene through conversion of the hydroxyl group into a leaving group and elimination, and finally hydrolysis of the resulting acetal, in this order. In each step of the elimination reaction and the hydrolysis reaction after the step of reduction reaction, isomerization scarcely occurs so that a high-purity terminal conjugated dienal compound can be synthesized. Further, in the reduction reaction step to the final hydrolysis reaction step, since impurities requiring isolation or purification operation are not produced, the terminal conjugated dienal compound obtained as a final product can be purified only by distillation.

Thus, according to the invention, there can be provided a method of producing an E or Z isomer of the terminal conjugated dienal compound with a good purity and in good yield without use of an oxidation reaction. In addition, according to the invention, there can be provided the hydroxyalkynal acetal compound (3), the (E)-hydroxyalkenal acetal compound (4), and the (Z)-hydroxyalkenal acetal compounds (8) and (8m), each being an intermediate useful for production of the terminal conjugated dienal compound.

DETAILED DESCRIPTION OF THE PREFERRED EMBODIMENTS

Embodiments of the invention will hereinafter be described in detail. It should not be construed that the invention is limited to or by the embodiments.

First, production of an (E)-dienal compound represented by formula (7), such as (E)-11,13-tetradecadienal, will be explained. In formula (7), n is an integer of from 2 to 11.

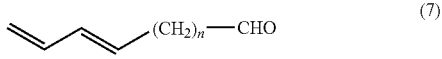 (7)

According to the invention, the starting material is an alkynal acetal compound represented by formula (1), which is synthesized by a known method. In formula (1), n is an integer of from 2 to 11 and $R^1$ and $R^2$ each independently represents a monovalent hydrocarbon group having from 1 to 10 carbon atoms, or $R^1$ and $R^2$ are coupled together to form a divalent hydrocarbon group having from 2 to 10 carbon atoms.

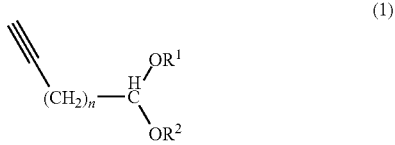 (1)

The monovalent hydrocarbon group of $R^1$ or $R^2$ may be exemplified by a monovalent hydrocarbon group having from 1 to 10 carbon atoms, preferably from 1 to 5 carbon atoms. Examples of the monovalent hydrocarbon group include linear or branched saturated hydrocarbon groups such as methyl, ethyl, n-propyl, n-butyl, n-pentyl and isopropyl; linear or branched unsaturated hydrocarbon groups such as 2-propenyl, 2-methyl-2-propenyl and 2-propynyl; and cyclic hydrocarbon groups such as cyclopropyl, 2-methylcyclopropyl, cyclobutyl and cyclopentyl. Monovalent hydrocarbon groups having isomeric relationship therewith may also be included. Part of hydrogen atoms of these hydrocarbon groups may be substituted by a methyl group, an ethyl group or the like. Of these examples, a methyl group, an ethyl, group, an n-propyl group and the like are particularly preferred from the standpoint of the reactivity in deprotection or purification ease, because they have high reactivity and by-products formed by the deprotection can easily be removed by washing with water or concentration of the reaction product.

Next, the divalent hydrocarbon group having from 2 to 10 carbon atoms formed by coupling of $R^1$ and $R^2$ will be explained. The divalent hydrocarbon group may be exemplified by a divalent hydrocarbon group having from 2 to 10 carbon atoms, preferably from 2 to 6 carbon atoms. Examples of the divalent hydrocarbon group include linear or branched saturated hydrocarbon groups such as ethylene, 1,2-propylene, 1,3-propylene, 2,2,-dimethyl-1,3-propylene, 1,2-butylene, 1,3-butylene, 1,4-butylene, 2,3-butylene and 2,3-dimethyl-2,3-butylene; linear or branched, unsaturated hydrocarbon groups such as 1-vinylethylene, 2-methylene-1,3-propylene and (Z)-2-butene-1,4-diyl; and cyclic hydrocarbon groups such as 1,2-cyclopropylene, 1,2-cyclobutylene, 1,2-cyclopentylene, 1,2-cyclohexylene and 1,2-phenylene. Divalent hydrocarbon groups having isomeric relationship therewith may also be included. Part of the hydrogen atoms of these hydrocarbon groups may be substituted by a methyl group, an ethyl group or the like. Of these examples, an ethylene group, an 1,2-propylene group, an 1,3-propylene group and the like are particularly preferred from the standpoint of the reactivity in deprotection, purification ease or easy availability.

Next, the step of metalizing the alkynal acetal compound (1) through a metalation reaction to obtain an organic metal compound represented by formula (2) below will be explained. In formula (2), n, $R^1$ and $R^2$ are the same as described above, respectively. M is a cationic moiety.

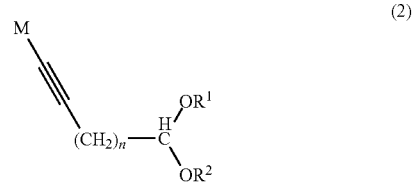 (2)

The organic metal compound (2) can be obtained by metalation of the alkynal acetal compound (1) serving as a substrate with a metal reagent of preferably from 0.01 to 1000 mol, more preferably from 0.1 to 100 mol, relative to 1 mol of the compound (1), in the presence or absence of a solvent and with optional heating or cooling.

The cationic moiety M is preferably a metal-containing cationic moiety. Examples of the cationic moiety M particularly preferably include Na, Li, MgX, ZnX, Cu and CuX wherein X is a halogen atom such as a chlorine atom, a bromine atom or an iodine atom.

The metal reagent to be used for the metalation is exemplified by a single-element metal such as sodium, and an organic metal reagent. Examples of the organic metal reagent include an organic lithium reagent such as methyllithium, ethyllithium, n-propyllithium, n-butyllithium, 2-propenyllithium, isopropenyllithium, lithium hexamethyldisilazide and lithium diisopropylamide; and an organic magnesium reagent such as methylmagnesium chloride, methylmagnesium bromide, methylmagnesium iodide, ethylmagnesium chloride, ethylmagnetium bromide, ethylmagnesium iodide, n-propylmagnesium chloride, n-propylmagnesium bromide and n-propylmagnesium iodide. Of these examples, n-butyllithium and methylmagnesium chloride are preferred.

The solvent to be used for the metalation is not particularly limited insofar as the solvent does not react with the organic metal compound (2). Examples of the solvent preferably include hydrocarbons such as hexane, heptane, benzene, toluene, xylene and cumene; and ethers such as diethyl ether, dibutyl ether, tetrahydrofuran and 1,4-dioxane. The solvent may be used singly or in combination of two or more. The amount of the solvent to be used for the metalation is preferably from 1 g to 10,000 g relative to 1 mol of the alkynal acetal compound (1) serving as a substrate.

The temperature of the metalation reaction depends on the kind of the metal element or a preparation method of the metal reagent. It is preferably from −78° C. to 120° C., more preferably from −50° C. to 100° C., still more preferably from −30° C. to 80° C.

The reaction time of the metalation may be selected arbitrarily. It is typically from about 0.5 to 72 hours.

Next, the step of reacting the organic metal compound (2) with ethylene oxide through an addition reaction to obtain a hydroxyalkynal acetal compound represented by formula (3) will be explained. In formula (3), n, $R^1$ and $R^2$ are the same as described above, respectively.

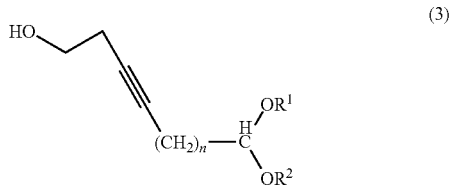

(3)

The hydroxyalkynal acetal compound (3) can be synthesized through an addition reaction by reacting the organic metal compound (2) serving as a substrate with ethylene oxide of preferably from 1 to 1000 mol, more preferably from 1 to 100 mol, relative to 1 mol of the substrate, in the presence or absence of a solvent and with optional heating or cooling.

The solvent to be used for the addition reaction is not particularly limited insofar as the solvent does not react with the organic metal compound (2). Examples of the solvent preferably include hydrocarbons such as hexane, heptane, benzene, toluene, xylene and cumene; and ethers such as diethyl ether, dibutyl ether, tetrahydrofuran and 1,4-dioxane. The solvent may be used singly or in combination of two or more. The amount of the solvent to be used for the addition reaction is preferably from 10 g to 10,000 g relative to 1 mol of the organic metal compound (2) serving as a substrate.

The reaction temperature of the addition reaction is preferably at from −78° C. to 120° C., more preferably from 0° C. to 100° C.

The reaction time of the addition reaction can be selected arbitrarily. It is desirable from the standpoint of the yield to monitor the reaction by gas chromatography (GC) or silica gel thin-layer chromatography (TLC) to complete the reaction. The reaction time is typically from about 0.5 to 72 hours. Isolation and purification of the intended hydroxyalkynal acetal compound (3) can be carried out by a method appropriately selected from the typical purification methods used in organic syntheses, such as distillation under reduced pressure and various types of chromatography. The distillation under reduced pressure is preferred from the standpoint of industrial economy. Examples of the compound of the formula (3) include 11-hydroxy-8-undecynal diethyl acetal and 14-hydroxy-11-tetradecynal diethyl acetal.

Next, the step of reducing of the hydroxyalkynal acetal compound (3) through a reduction reaction to obtain an (E)-hydroxyalkenal acetal compound represented by formula (4) below will be explained. In formula (4), n, $R^1$ and $R^2$ are the same as described above, respectively.

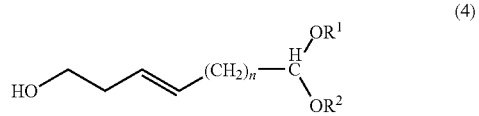

(4)

The (E)-hydroxyalkenal acetal compound (4) can be synthesized by reduction of the hydroxyalkynal acetal compound (3) serving as a substrate with a reducing agent in the presence or absence of a solvent and with optional heating or cooling.

Examples of the reduction reaction include a catalytic hydrogenation reaction using hydrogen as a reducing agent and a reduction reaction with a metal hydride. Of these examples, the reduction reaction with a metal hydride is preferred.

Examples of the hydrogenation reducing agent (i.e. metal hydride) to be used in the reduction reaction with a metal hydride include aluminum hydride, lithium aluminum hydride, lithium boron hydride and diborane. The lithium aluminum hydride is preferred. The amount of the metal hydride to be used for the reduction reaction is preferably from 0.01 to 100 mol, more preferably from 0.1 to 50 mol, relative to 1 mol of the hydroxyalkynal acetal compound (3) serving as a substrate.

The solvent to be used for the reduction reaction is variable depending on the kind of the reducing agent. Examples of the solvent preferably include hydrocarbons such as hexane, heptane, benzene, toluene, xylene and cumene; and ethers such as diethyl ether, dibutyl ether, tetrahydrofuran, 1,4-dioxane and diglyme. The solvent may be used singly or in combination of two or more. The amount of the solvent to be used for the reduction reaction is preferably from 10 g to 10,000 g relative to 1 mol of the hydroxyalkynal acetal compound (3) serving as a substrate.

The reaction temperature of the reduction reaction is preferably from −78° C. to the boiling point of the solvent, more preferably from −10° C. to 200° C.

The reaction time of the reduction reaction can be selected arbitrarily. It is desirable from the standpoint of the yield to monitor the reaction by gas chromatography (GC) or silica gel thin-layer chromatography (TLC) to complete the reaction. The reaction time is typically from about 0.5 to 72 hours. The (E)-hydroxyalkenal acetal compound (4) thus obtained can be provided for a subsequent step as a crude product without particular purifying operation. However, when purification is carried out, it can be carried out by a method selected from the typical purification methods used in organic syntheses, such as distillation under reduced pressure and various types of chromatography. The distillation under reduced pressure is preferred from the standpoint of industrial economy. Examples of the compound of the formula (4) include (E)-14-hydroxy-11-tetradecenal diethyl acetal.

Next, the step of converting the (E)-hydroxyalkenal acetal compound (4) through a functional group conversion reaction into an (E)-alkenal acetal compound having a leaving group X represented by formula (5) below will be explained. In formula (5), n, $R^1$ and $R^2$ are the same as described above, respectively, and X is a leaving group.

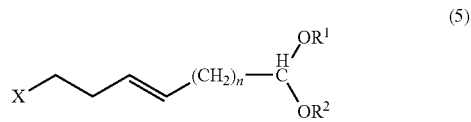

(5)

Examples of the leaving group X include a halogen atom such as chlorine and bromine; a substituted or unsubstituted alkanesulfonyloxy group such as methanesulfonyloxy, ethanesulfonyloxy and trifluoromethanesulfonyloxy; and an arenesulfonyloxy group such as benzenesulfonyloxy and toluenesulfonyloxy. For example, the chlorine atom and the methanesulfonyloxy group are preferred.

When the halogen atom is used as the leaving group, examples of a halogenating agent include a thionyl halide such as thionyl chloride and thionyl bromide; a phosphorus halide compound such as phosphorus trichloride, phosphorus tribromide, phosphorus pentachloride and phosphorus pentabromide; a phosphorus oxyhalide compound such as phosphorus oxychloride and phosphorus oxybromide; and an aromatic phosphorus halide compound such as dichlorotriphenylphosphorane and dibromotriphenylphosphorane. When a sulfonic halide such as methanesulfonyl chloride, ethanesulfonyl chloride or trifluoromethanesulfonyl chloride is used, the hydroxyl group of the (E)-hydroxyalkenal acetal compound (4) is sulfonated by the sulfonic halide, and then the sulfonyloxy group can be replaced by the halogen atom corresponding to the sulfonic halide with optional heating.

When the substituted or unsubstituted alkanesulfonyloxy group is used as the leaving group, examples of an alkanesulfonating agent include a substituted or unsubstituted alkanesulfonic acid such as methanesulfonic acid, ethanesulfonic acid and trifluoromethanesulfonic acid; a substituted or unsubstituted alkanesulfonic anhydride such as methanesulfonic anhydride, ethanesulfonic anhydride and trifluoromethanesulfonic anhydride; and a substituted or unsubstituted alkanesulfonic halide such as methanesulfonyl chloride, ethanesulfonyl chloride and trifluoromethanesulfonyl chloride.

When the arenesulfonyloxy group is used as the leaving group, examples of an arenesulfonating agent include an arenesulfonic acid such as benzenesulfonic acid and p-toluenesulfonic acid; an arenesulfonic anhydride such as benzenesulfonic anhydride and p-toluenesulfonic anhydride; and an arenesulfonic halide such as benzenesulfonyl chloride and p-toluenesulfonyl chloride.

The functional group conversion reaction is preferably carried out under basic or weakly acidic conditions because the acetal serving as a substrate may be decomposed by the reaction under strongly acidic conditions. Preferred examples include the reaction using a sulfonic halide as the halogenating agent and a base.

The base is exemplified by an organic base and an inorganic base. Examples of the organic base include amines such as diethylamine, triethylamine, diisopropylethylamine, tri-n-propylamine, tri-n-butylamine, diazabicyclononene (DBN), diazabicycloundecene (DBU), N-methylmorpholine and N,N-dimethylaniline; pyridines such as pyridine, methylethylpyridine, lutidine and N,N-dimethyl-4-aminopyridine; imidazoles; and pyrazoles. Examples of the inorganic base include a hydroxide of alkali metal or alkaline earth metal such as lithium hydroxide, sodium hydroxide, potassium hydroxide, magnesium hydroxide, calcium hydroxide and barium hydroxide; a carbonate of alkali metal or alkaline earth metal such as sodium carbonate, potassium carbonate, cesium carbonate, magnesium carbonate, calcium carbonate and barium carbonate; a metal alkoxide such as sodium ethoxide; an alkali metal amide such as sodium amide and lithium amide; and an alkali metal hydride such as sodium hydride and lithium hydride. Preferable examples of the base include pyridine and triethylamine.

Examples of the solvent to be used in the functional group conversion reaction preferably include hydrocarbons such as hexane, heptane, benzene, toluene, xylene and cumene; ethers such as diethyl ether, dibutyl ether, tetrahydrofuran and 1,4-dioxane; chlorine-based solvents such as methylene chloride, chloroform and trichloroethylene; ketones such as acetone, methyl butyl ketone and methyl isobutyl ketone; aprotic polar solvents such as N,N-dimethylformamide (DMF), 1,3-dimethyl-2-imidazolidinone (DMI), dimethyl sulfoxide (DMSO) and hexamethylphosphoric triamide (HMPA); and nitriles such as acetonitrile and butyronitrile. The base may be used singly or in combination of two or more. The solvent is used preferably in an amount of from 10 to 10,000 g relative to 1 mol of the (E)-hydroxyalkenal acetal compound (4) serving as a substrate.

The reaction temperature of the functional group conversion reaction is variable depending on the reaction conditions. It is preferably from −78° C. to the boiling point of the solvent, more preferably from −10° C. to 100° C.

The reaction time of the functional group conversion reaction can be selected arbitrarily. It is desirable from the standpoint of the yield to monitor the reaction by gas chromatography (GC) or silica gel thin-layer chromatography (TLC) to complete the reaction. The reaction time is typically from about 0.5 to 72 hours. The obtained (E)-alkenal acetal compound (5) having a leaving group can be provided for a subsequent step as a crude product without particular purifying operation. However, when purification is carried out, it can be carried out by a method appropriately selected from the typical purification methods used in organic syntheses, such as distillation under reduced pressure or various types of chromatography. The distillation under reduced pressure is preferred from the standpoint of industrial economy.

Next, the step of an elimination reaction of the (E)-alkenal acetal compound (5) having a leaving group X to obtain an (E)-dienal acetal compound represented by formula (6) below will be explained. In formula (6), n, R¹ and R² are the same as described above, respectively.

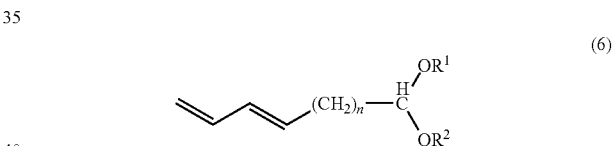

(6)

The (E)-dienal acetal compound (6) can be synthesized by eliminating HX from the substrate (5) in the presence of preferably from 0.01 to 100 mol of a base, relative to 1 mol of the (E)-alkenal acetal compound (5) having a leaving group, and in the presence or absence of a solvent with optional heating or cooling.

Examples of the base to be used for the elimination reaction include alkoxides such as sodium methoxide, sodium ethoxide, sodium t-butoxide, sodium t-amyloxide, lithium methoxide, lithium ethoxide, lithium t-butoxide, lithium t-amyloxide, potassium methoxide, potassium ethoxide, potassium t-butoxide and potassium t-amyloxide; hydroxides such as sodium hydroxide, lithium hydroxide, potassium hydroxide and barium hydroxide; carbonates such as sodium carbonate, potassium carbonate, sodium bicarbonate and potassium bicarbonate; organic metal reagents such as methyllithium, ethyllithium, n-butyllithium and methylmagnesium chloride; metal amides such as lithium diisopropylamide, lithium hexamethyldisilazide, sodium hexamethyldisilazide and lithium dicyclohexylamide; metal hydrides such as sodium hydride, potassium hydride and calcium hydride; and organic bases such as triethylamine, diisopropyloethylamine, tributylamine, N,N-dimethylaniline, N,N-diethylaniline, pyridine, 4-dimethylaminopyridine, quinolone, pyrrolidine, piperidine, collidine, lutidine, morpholine and piperazine. The base may be used singly or in combination of two or more. The base can be selected in consideration of the kind of the substrate, reactivity and/or selectivity. Of these bases, carbonates such as potassium carbonate are preferred.

Examples of the solvent to be used for the elimination reaction include water; alcohols such as methanol, ethanol, isopropyl alcohol, t-butyl alcohol, benzyl alcohol, methoxyethanol and ethoxyethanol; ethers such as diethyl ether, dibutyl ether, tetrahydrofuran and 1,4-dioxane; hydrocarbons such as hexane, heptane, benzene, toluene, xylene and cumene; aprotic polar solvents such as N,N-dimethylformamide (DMF), 1,3-dimethyl-2-imidazolidinone (DMI), dimethyl sulfoxide (DMSO) and hexamethylphosphoric triamide (HMPA); and nitriles such as acetonitrile and propionitrile. The solvent may be used singly or in combination of two or more. With regards to the selection of the base and the solvent, the conditions in the reaction system are presumed to be equal between use of an alkoxide as a base in a water-containing solvent and use of a hydroxide as a base in an alcohol-containing solvent.

The reaction temperature of the elimination reaction is preferably from −78° C. to the boiling point of the solvent, more preferably from −10° C. to 100° C.

The reaction time of the elimination reaction can be selected arbitrarily. It is desirable from the standpoint of the yield to monitor the reaction by gas chromatography (GC) or silica gel thin-layer chromatography (TLC) to complete the reaction. The reaction time is typically from about 0.5 to 72 hours. The obtained (E)-dienal acetal compound (6) can be provided for a subsequent step as a crude product without particular purifying operation. However, when purification is carried out, it can be carried out by a method appropriately selected from the typical purification methods used in organic syntheses such as distillation under reduced pressure and various types of chromatography. The distillation under reduced pressure is preferred from the standpoint of industrial economy.

Next, the step of hydrolyzing the (E)-dienal acetal compound (6) through a hydrolysis reaction to obtain an (E)-dienal compound represented by formula (7) below will be explained. In formula (7), n is the same as described above.

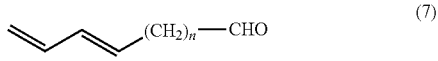
(7)

The (E)-dienal compound (7) can be synthesized by mixing the (E)-dienal acetal compound (6) with an acid, water and an optional solvent with optional cooling or heating.

Examples of the acid to be used for the hydrolysis include inorganic acids or salts thereof such as hydrochloric acid, hydrobromic acid, hydroiodic acid, sulfuric acid, nitric acid, phosphoric acid, and salts thereof; organic acids or salts thereof such as formic acid, acetic acid, propionic acid, oxalic acid, trifluoroacetic acid, methanesulfonic acid, benzenesulfonic acid, p-toluenesulfonic acid, naphthalenesulfonic acid, and salts thereof; Lewis acids such as lithium tetrafluoroborate, boron trifluoride, boron trichloride, boron tribromide, aluminum trichloride, zinc chloride, zinc bromide, zinc iodide, tin tetrachloride, tin tetrabromide, tin dichloride, titanium tetrachloride, titanium tetrabromide and trimethylsilyl iodide; oxides such as alumina, silica gel and titania; and minerals such as montmorillonite. The acid may be used singly or in combination of two or more. The acid is used preferably in a small amount from the standpoint of economy, and the amount of the acid can be selected arbitrarily insofar as a reaction rate adequate in practical use can be attained. The acid is preferably from 0.00001 mol to 10,000 mol, more preferably from 0.0001 mol to 1,000 mol, still more preferably from 0.001 mol to 100 mol, relative to 1 mol of the (E)-dienal acetal compound (6) serving as a substrate.

The greater the amount of water to be used in hydrolysis is, the more efficient the reaction becomes because the equilibrium shifts to the formation side of the aldehyde. From the standpoint of the economy, workability, yield and the like, the water is added preferably in an amount of from 1 mol to 10,000 mol, more preferably from 1 mol to 1,000 mol, still more preferably from 1 mol to 500 mol, relative to 1 mol of the (E)-dienal acetal compound (6) serving as a substrate. The reaction may be carried out while removing from the reaction system an alcohol produced during the hydrolysis of the acetal, using a method such as distillation or phase separation.

Examples of the solvent to be used in the hydrolysis include ethers such as diethyl ether, dibutyl ether, tetrahydrofuran and 1,4-dioxane; hydrocarbons such as hexane, heptane, benzene, toluene, xylene and cumene; chlorine-based solvents such as methylene chloride, chloroform and trichloroethylene; ketones such as acetone and methyl ethyl ketone; aprotic polar solvents such as N,N-dimethylformamide (DMF), 1,3-dimethyl-2-imidazolidinone (DMI), dimethyl sulfoxide (DMSO) and hexamethylphosphoric triamide (HMPA); and nitriles such as acetonitrile and propionitrile; esters such as ethyl acetate and n-butyl acetate; and alcohols such as methanol, ethanol and t-butyl alcohol. The solvent may be used singly or in combination of two or more. The solvent to be used for deprotection (i.e. hydrolysis) is preferably in an amount of from 10 g to 10,000 g relative to 1 mol of the (E)-dienal acetal compound (6) serving as a substrate.

The reaction temperature of the hydrolysis reaction is variable depending on reaction conditions. The reaction temperature is preferably from −78° C. to 160° C., more preferably from −50° C. to 140° C., still more preferably from −30° C. to 120° C.

The reaction time of the hydrolysis reaction can be selected arbitrarily. It is desirable from the standpoint of the yield to monitor the reaction by gas chromatography (GC) or silica gel thin-layer chromatography (TLC) to complete the reaction. The reaction time is typically from about 0.5 to 24 hours. The isolation and purification of the intended (E)-dienal compound (7) can be carried out by a method appropriately selected from the typical purification methods used in organic syntheses such as distillation under reduced pressure and various types of chromatography. The distillation under reduced pressure is preferred from the standpoint of industrial economy.

Next, a method for producing a (Z)-dienal compound represented by formula (11) below such as (Z)-11,13-tetradecadienal will be explained. In formula (11), n is the same as described above.

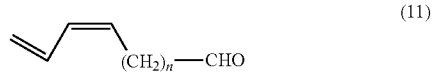
(11)

A method of producing a hydroxyalkynal acetal compound (3) is the same as the above-described method, and comprises the steps of: metalizing an alkynal acetal compound represented by formula (1) through a metalation reaction to obtain an organic metal compound represented by formula (2) and reacting the obtained organic compound with ethylene oxide through an addition reaction to obtain a hydroxyalkynal acetal compound represented by formula (3).

Next, the step of reducing the hydroxyalkynal acetal compound (3) through a reduction reaction to obtain a (Z)-hydroxyalkenal acetal compound represented by formula (8) below will be explained. In formula (8), n, $R^1$ and $R^2$ are the same as described above, respectively.

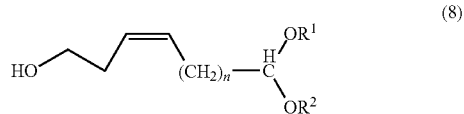

The (Z)-hydroxyalkenal acetal compound (8) can be synthesized from the hydroxyalkynal acetal compound (3) serving as a substrate with a reducing agent through selective reduction of the triple bond into a Z-alkene.

Examples of the reduction reaction include a catalytic hydrogenation reaction with hydrogen as a reducing agent and a reduction reaction with a hydrogenation reducing agent. Preferable examples thereof include the catalytic hydrogenation reaction with hydrogen.

The catalytic hydrogenation reaction is typically carried out with optional cooling or heating in the presence of a catalyst in a hydrogen atmosphere, in the presence or absence of a solvent and in a homogeneous or heterogeneous system.

Examples of the catalyst in the catalytic hydrogenation reaction include metals such as cobalt, nickel, rhodium, palladium, ruthenium, osmium, platinum, iridium, copper and iron; and oxides, hydroxides and halides of the metals. The catalyst may be used singly or in combination of two or more. Examples of a carrier on which the above-exemplified metal catalyst will be deposited include calcium carbonate, carbon, alumina, zeolite and silica gel. Of these examples, a Lindlar catalyst having a palladium catalyst deposited on calcium carbonate and having catalytic activity reduced by poisoning with lead acetate or the like, is preferred.

Examples of the solvent to be used in the catalytic hydrogenation reaction include alcohols such as methanol, ethanol, isopropyl alcohol, t-butyl alcohol, benzyl alcohol, methoxyethanol and ethoxyethanol; ethers such as diethyl ether, dibutyl ether, tetrahydrofuran and 1,4-dioxane; hydrocarbons such as hexane, heptane, benzene, toluene, xylene and cumene; aprotic polar solvents such as N,N-dimethylformamide (DMF), 1,3-dimethyl-2-imidazolidinone (DMI), dimethyl sulfoxide (DMSO) and hexamethylphosphoric triamide (HMPA); and nitriles such as acetonitrile and propionitrile. The solvent may be used singly or in combination of two or more.

The hydrogen pressure in the catalytic hydrogenation reaction is preferably from normal pressure to 5 MPa. The reaction temperature is preferably from 5° C. to 70° C., more preferably from 20° C. to 50° C.

The reaction time of the catalytic hydrogenation reaction can be selected arbitrarily. It is desirable from the standpoint of the yield to monitor the reaction by gas chromatography (GC) or thin-layer chromatography (TLC) to complete the reaction. The reaction time is typically from about 0.5 to 72 hours. The obtained (Z)-hydroxyalkenal acetal compound (8) can be provided for a subsequent step as a crude product without particular purifying operation. However, when purification is carried out, it can be carried out by a method appropriately selected from the typical purification methods used in organic syntheses, such as distillation under reduced pressure and various types of chromatography. The distillation under reduced pressure is preferred from the standpoint of industrial economy. Examples of the compound of formula (8) include (Z)-11-hydroxy-8-undecenal diethyl acetal and (Z)-14-hydroxy-11-tetradecenal diethyl acetal.

The step of a functional group conversion reaction of the (Z)-hydroxyalkenal acetal compound (8) to obtain a (Z)-alkenal acetal compound having a leaving group X represented by formula (9) below is the similar to the step of the functional group conversion reaction of the (E)-hydroxyalkenal acetal compound represented by formula (4) to obtain the (E)-alkenal acetal compound having a leaving group X represented by formula (5). In formula (9), n, $R^1$, $R^2$ and X are the same as described above, respectively.

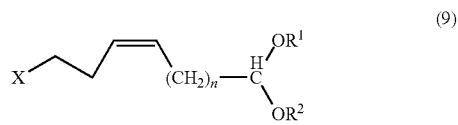

The step of an elimination reaction of the (Z)-alkenal acetal compound (9) having a leaving group X to obtain a (Z)-dienal acetal compound represented by formula (10) below is similar to the step of the elimination reaction of the (E)-alkenal acetal compound having a leaving group X represented by formula (5) to obtain the (E)-dienal acetal compound represented by formula (6). In formula (10), n, $R^1$ and $R^2$ are the same as described above, respectively.

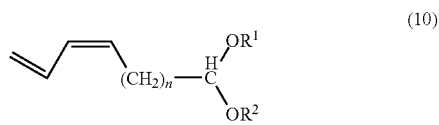

The step of hydrolyzing the (Z)-dienal acetal compound (10) through a hydrolysis reaction to obtain a (Z)-dienal compound represented by formula (11) below is similar to the step of hydrolyzing the (E)-dienal acetal compound represented by formula (6) through the hydrolysis reaction to obtain the (E)-dienal compound represented by formula (7). In formula (11), n is the same as described above.

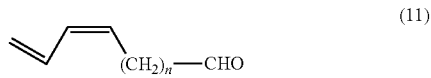

As described above, a method of producing the E isomer or Z isomer of a terminal conjugated dienal compound with a high purity and in high yield can thus be provided to supply a sufficient amount of product for applications or utilizations. In addition, a hydroxyalkynal acetal compound (3), an (E)-hydroxyalkenal acetal compound (4) and (Z)-hydroxyalkenal acetal compounds (8) and (8m), each being an intermediate useful for the production of a terminal conjugated dienal compound, can be provided. The compound (8m) is the same as the compound (8) except that the former contains m in the place of n, wherein n is an integer of from 2 to 11, while m is an integer of from 5 to 11.

EXAMPLES

The invention will hereinafter be described more specifically with reference to Examples. It should not be construed that the invention is limited to or by Examples.

Example 1

<Synthesis of Organic Metal Compound (2) Through Metalation of 8-nonynal diethyl acetal (1)> (n=6, $R^1$=$CH_2CH_3$, $R^2$=$CH_2CH_3$, and Methylmagnesium Chloride as the Metal Reagent)

In a nitrogen atmosphere, a solution of methylmagnesium chloride (38.59 g:0.516 mol) in tetrahydrofuran (160.99 g) was placed in a reactor, and stirred at a solution temperature of 50 to 55° C. The resulting solution was subjected to dropwise addition of 8-nonynal diethyl acetal (1) (89.03 g:0.3967 mol) at a solution temperature of 55 to 60° C. over 30 minutes, and then stirred at 60 to 65° C. for 6 hours. The reaction solution was cooled to 55° C. or less and provided for a subsequent step.

Example 2

<Synthesis of 11-hydroxy-8-undecynal diethyl acetal (3)> (n=6, $R^1$=$CH_2CH_3$ and $R^2$=$CH_2CH_3$)

The solution of the organic metal compound (2) prepared in Example 1 was subjected to dropwise addition of ethylene oxide (27.93 g:0.635 mol) at a reaction solution temperature of 50 to 60° C. over 45 minutes, and then stirred at 50 to 60° C. for 3 hours. The reaction solution was cooled to 50° C. or less, subjected to addition of pure water (500 g), acetic acid (48 g) and hexane (100 g), and then stirred for 30 minutes. The organic phase separated was subjected to typical work-up of washing, drying and concentration to obtain an intended crude product (110.01 g). The crude product was distilled under reduced pressure to obtain the intended 11-hydroxy-8-undecynal diethyl acetal (3) (85.56 g:0.558 mol). The total yield of those two steps calculated based on the sum of "weight multiplied by purity" with respect to all the fractions including the fractions obtained in the previous distillation was 91.98%.

11-Hydroxy-8-undecynal diethyl acetal (3)

Colorless to pale yellow oily liquid
IR (D-ATR): ν=3449, 2974, 2931, 2859, 1443, 1374, 1345, 1128, 1056, 849, 724 $cm^{-1}$.
$^1$H-NMR (500 MHz, $CDCl_3$): δ=1.18 (6H, t, J=7.1 Hz), 1.21-1.38 (6H, m), 1.46 (2H, quin, J=7.2 Hz), 1.56-1.60 (2H, m), 2.13 (2H, tt, J=2.3, 7.1 Hz), 2.40 (2H, tt, J=2.3, 6.2 Hz), 3.42-3.53 (2H, m), 3.57-3.71 (4H, m), 4.45 (1H, t, J=6.0 Hz) ppm.
$^{13}$C-NMR (125 MHz, $CDCl_3$): δ=15.29, 18.64, 23.09, 24.55, 28.69, 28.79, 28.89, 33.45, 60.78, 61.28, 76.34, 82.48, 102.84 ppm.
GC-MS (EI, 70 eV): 29, 43, 57, 75, 89, 103, 121, 137, 151, 165, 181, 195, 211, 227, 255, 281 ($M^+$).

Example 3

<Synthesis of Organic Metal Compound (2) Through Metalation of 11-dodecynal diethyl acetal (1)> (n=9, $R^1$=$CH_2CH_3$, $R^2$=$CH_2CH_3$, and Methyl Magnesium Chloride as the Metal Reagent)

In a nitrogen atmosphere, a solution of methylmagnesium chloride (63.05 g:0.843 mol) in tetrahydrofuran (263.16 g) was placed in a reactor, and stirred at a solution temperature of 50 to 55° C. The resulting solution was subjected to dropwise addition of 11-dodecynal diethyl acetal (1) (196.84 g:0.6484 mol) at a solution temperature of 55 to 60° C. over one hour, and then stirred at 60 to 65° C. for 6 hours. The reaction solution was cooled to 55° C. or less and provided for a subsequent step.

Example 4

<Synthesis of 14-hydroxy-11-tetradecynal diethyl acetal> (n=9, $R^1$=$CH_2CH_3$, and $R^2$=$CH_2CH_3$)

The solution of the organic metal compound (2) prepared in Example 3 was subjected to dropwise addition of ethylene oxide (69.65 g:1.583 mol) at a reaction solution temperature of 50 to 60° C. over 30 minutes, and then stirred at 50 to 60° C. for 3 hours. The reaction solution was cooled to 50° C. or less, subjected to addition of pure water (810 g), acetic acid (98.36 g) and hexane (100 g), and then stirred for 30 minutes. The organic phase separated was subjected to typical work-up of washing, drying and concentration to obtain an intended crude product (233.15 g). The crude product was distilled under reduced pressure to obtain the intended 14-hydroxy-11-tetradecynal diethyl acetal (3) (189.32 g:0.558 mol). The total yield of those two steps calculated based on the sum of "weight multiplied by purity" with respect to all the fractions including the factions obtained in the previously distillation was 92.69%.

14-Hydroxy-11-tetradecynal diethyl acetal (3)

Colorless to pale yellow oily liquid
IR (D-ATR): ν=3418, 2974, 2928, 2855, 1457, 1444, 1374, 1344, 1127, 1055, 850, 725 $cm^{-1}$.
$^1$H-NMR (500 MHz, $CDCl_3$): δ=1.18 (6H, t, J=7.1 Hz), 1.23-1.39 (12H, m), 1.46 (2H, quin, J=7.3 Hz), 1.56-1.60 (2H, m), 1.97-1.99 (1H, m), 2.14 (2H, tt, J=2.4, 7.1 Hz), 2.41 (2H, tt, J=2.5, 6.3 Hz), 3.44-3.50 (2H, m), 3.58-3.67 (4H, m), 4.46 (1H, t, J=5.8 Hz) ppm.
$^{13}$C-NMR (125 MHz, $CDCl_3$): δ=15.30, 18.67, 23.11, 24.69, 28.77, 28.91, 29.03, 29.35, 29.39, 29.42, 33.52, 60.77, 61.31, 76.23, 82.64, 102.91 ppm.
GC-MS (EI, 70 eV): 29, 47, 61, 75, 89, 103, 121, 147, 161, 175, 189, 207, 225, 239, 253, 269, 297 ($M^+$).

Example 5

<Synthesis of (E)-14-hydroxy-11-tetradecenal diethyl acetal (4)> (n=9, $R^1$=$CH_2CH_3$, $R^2$=$CH_2CH_3$, and Lithium Aluminum Hydride as the Reducing Agent)

In a nitrogen atmosphere, lithium aluminum hydride (1.68 g:0.044 mol) and diglyme (60 g) were placed in a reactor, and stirred at a solution temperature of 20 to 30° C. for 2 hours. The resulting solution was subjected to dropwise addition of 14-hydroxy-11-tetradecynal diethyl acetal (3)

(15.00 g:0.047 mol) at a solution temperature of 20 to 40° C. over 15 minutes, and then stirred at 130 to 140° C. for 6 hours. The reaction solution was cooled to 40° C. or less, and subjected to addition of tetrahydrofuran (200 g). The resulting reaction solution was subjected to dropwise addition of pure water (1.68 g) at a solution temperature of 20 to 25° C. over 5 minutes, and stirred for one hour. Then the solution was subjected to dropwise addition of a 15% NaOH solution (1.68 g) at a solution temperature of 20 to 25° C. over 5 minutes, and then stirred for one hour. The reaction solution was subjected to dropwise addition of pure water (5.04 g) at a solution temperature of 20 to 25° C. over 5 minutes, and then stirred for one hour. The solution was subjected to addition of Celite® (33 g) at a solution temperature of from 20 to 25° C., and stirred for 30 minutes. A filtrate obtained by filtering the solution to remove the solid matter was subjected to typical work-up of washing, drying and concentration to obtain an the intended (E)-14-hydroxy-11-tetradecenal diethyl acetal (4) (14.98 g:0.043 mol). The E:Z ratio of the product was 100:0 and the yield was 92.4%.

(E)-14-Hydroxy-11-tetradecenal diethyl acetal (4)

Colorless to pale yellow oily liquid
IR (D-ATR): ν=3445, 2975, 2925, 2854, 1457, 1443, 1374, 1345, 1127, 1056, 968, 722 $cm^{-1}$.
$^1$H-NMR (500 MHz, $CDCl_3$): δ=1.17 (6H, t, J=6.9 Hz), 1.21-1.36 (14H, m), 1.56-1.61 (3H, m), 1.99 (2H, q, J=6.9 Hz), 2.22-2.26 (2H, m), 3.44-3.50 (2H, m), 3.58-3.65 (4H, m), 4.46 (1H, t, J=5.9 Hz), 5.36 (1H, dt, J=5.4, 15.3 Hz), 5.53 (1H, dt, J=6.8, 15.3 Hz) ppm.
$^{13}$C-NMR (125 MHz, $CDCl_3$): δ=15.31, 24.70, 29.09, 29.39, 29.41, 29.45, 29.48, 32.62, 33.52, 35.95, 60.75, 61.98, 102.91, 125.67, 134.24 ppm.
GC-MS (EI, 70 eV): 25, 41, 57, 85, 103, 121, 149, 165, 192, 208, 224, 255, 281, 299 ($M^+$).

Example 6

<Synthesis of (E)-14-chloro-11-tetradecenal diethyl acetal (5)> (n=9, $R^1$=$CH_2CH_3$, $R^2$=$CH_2CH_3$, X=Cl, Methanesulfonyl Chloride as a Halogenating Agent, and the Pyridine as the Base)

In a nitrogen atmosphere, the (E)-14-hydroxy-11-tetradecenal diethyl acetal (4) (13.32 g:0.038 mol), pyridine (4.55 g:0.058 mol) and N,N-dimethylformamide (53.28 g) were placed in a reactor, and stirred at a solution temperature of 0 to 5° C. for 5 minutes. The resulting solution was subjected to dropwise addition of methanesulfonyl chloride (6.15 g:0.054 mol) at a solution temperature of 10° C. or less over one hour, and then stirred at a reaction solution temperature of 20 to 25° C. for 2 hours, and then at a reaction solution temperature of from 55 to 60° C. for 2 hours. The reaction solution thus obtained was cooled to 40° C. or less, subjected to addition of pure water (200 g) and n-hexane (200 g), and then stirred for 30 minutes. The organic phase separated was subjected to typical work-up of washing, drying and concentration to obtain the intended (E)-14-chloro-11-tetradecenal diethyl acetal (5) (10.17 g:0.029 mol). The yield was 76.32%.

(E)-14-Chloro-11-tetradecenal diethyl acetal (5)

Colorless to pale yellow oily liquid
IR (D-ATR): ν=2975, 2925, 2854, 1727, 1654, 1444, 1373, 1345, 1301, 1127, 1062, 969, 722, 660 $cm^{-1}$.
$^1$H-NMR (500 MHz, $CDCl_3$): δ=1.19 (6H, t, J=7.1 Hz), 1.22-1.38 (14H, m), 1.57-1.60 (2H, m), 1.94-2.01 (2H, m), 2.44 (2H, dq, J=0.9 Hz, 6.9 Hz), 3.42-3.60 (4H, m), 3.60-3.69 (2H, m), 4.47 (1H, t, J=5.7 Hz), 5.35-5.42 (1H, m), 5.50-5.56 (1H, m) ppm.
$^{13}$C-NMR (125 MHz, $CDCl_3$): δ=15.33, 24.71, 29.06, 29.25, 29.40, 29.44, 29.47, 29.50, 32.50, 33.55, 35.88, 44.46, 60.75, 102.92, 125.42, 134.04 ppm.
GC-MS (EI, 70 eV): 25, 41, 57, 85, 103, 119, 135, 157, 176, 192, 215, 236, 257, 273, 317 ($M^+$).

Example 7

Synthesis of (E)-11,13-tetradecadienal diethyl acetal (6)

In a nitrogen atmosphere, potassium t-butoxide (3.50 g:0.031 mol) and tetrahydrofuran (34.24 g) were placed in a reactor, and stirred at a solution temperature of 0 to 5° C. for 15 minutes. The resulting solution was subjected to dropwise addition of the (E)-14-chloro-11-tetradecenal diethyl acetal (5) (8.56 g:0.024 mol) at a solution temperature of 10° C. or less over 15 minutes, and then stirred at room temperature for 5 hours. The reaction solution was subjected to addition of pure water (200 g) and n-hexane (200 g), and then stirred for 30 minutes. The organic phase separated was subjected to typical work-up of washing, drying and concentration to obtain the intended (E)-11,13-tetradecadienal diethyl acetal (6) (7.25 g:0.023 mol). The yield was 95.83%.

(E)-11,13-Tetradecadienal diethyl acetal (6)

Colorless to pale yellow oily liquid
IR (D-ATR): ν=2974, 2925, 2854, 1653, 1603, 1465, 1373, 1345, 1127, 1061, 1002, 950, 895, 723 $cm^{-1}$.
$^1$H-NMR (500 MHz, $CDCl_3$): δ=1.20 (6H, t, J=7.1 Hz), 1.23-1.38 (14H, m), 1.57-1.61 (2H, m), 2.06 (2H, q, J=7.0 Hz), 3.44-3.51 (2H, m), 3.60-3.65 (2H, m), 4.47 (1H, t, J=5.8 Hz), 4.94 (1H, d, J=9.9 Hz), 5.07 (1H, d, J=16.5 Hz), 5.69 (1H, dt, J=7.3, 14.6 Hz), 6.03 (1H, dd, J=5.2, 15.1 Hz), 6.30 (1H, dt, J=10.2, 17.0 Hz) ppm.
$^{13}$C-NMR (125 MHz, $CDCl_3$): δ=15.33, 24.73, 29.16, 29.20, 29.38, 29.43, 29.46, 29.52, 33.56, 60.77, 102.93, 114.52, 130.81, 135.58, 137.33 ppm.
GC-MS (EI, 70 eV): 27, 41, 57, 71, 85, 103, 121, 136, 161, 175, 192, 207, 221, 236, 253, 282 ($M^+$).

Example 8

<Synthesis of (E)-11,13-tetradecadienal (7)> (n=9 and Oxalic Acid as the Acid)

In a nitrogen atmosphere, the (E)-11,13-tetradecadienal diethyl acetal (6) (5.85 g:0.019 mol), tetrahydrofuran (58.5 g), pure water (58.5 g) and oxalic acid dihydrate (2.81 g:0.022 mol) were placed in a reactor, and refluxed with stirring for 5 hours. The reaction solution was cooled to 40° C. or less, subjected to addition of sodium chloride (5.85 g) and n-hexane (100 g), and then stirred for 30 minutes. The organic phase separated was subjected to typical work-up of washing, drying and concentration to obtain 4.90 g of a crude product. The crude product was distilled under reduced pressure to obtain the intended (E)-11,13-tetradecadienal (7) (4.75 g:0.017 mol). The E:Z ratio of the product was 99:1 and the yield was 89.47%.

(E)-11,13-Tetradecadienal (7)

IR (D-ATR): ν=3085, 2925, 2854, 2716, 1726, 1652, 1602, 1464, 1004, 951, 896, 722 $cm^{-1}$.

¹H-NMR (500 MHz, CDCl₃): δ=1.25-1.42 (12H, m), 1.61 (2H, quin, J=7.3 Hz), 2.06 (2H, q, J=6.9 Hz), 2.41 (2H, dt, J=1.5, 7.5 Hz), 4.94 (1H, dd, J=1.1, 10.7 Hz), 5.07 (1H, dd, J=1.1, 16.5 Hz), 5.69 (1H, dt, J=7.3, 14.6 Hz), 6.03 (1H, dd, J=10.5, 15.1 Hz), 6.30 (1H, dt, J=10.2, 17.0), 9.75 (1H, t, J=2.0 Hz) ppm.

¹³C-NMR (125 MHz, CDCl₃): δ=22.01, 29.10, 29.29, 29.34, 32.48, 43.86, 114.54, 130.82, 135.51, 137.29, 202.90 ppm.

GC-MS (EI, 70 eV): 29, 41, 54, 67, 81, 95, 109, 121, 135, 151, 165, 179, 193, 208, 220 (M⁺).

Example 9

<Synthesis of (Z)-11-hydroxy-8-undecenal diethyl acetal (8)> (n=6, R¹=CH₂CH₃, R²=CH₂CH₃, and Hydrogenation Reaction with Lindlar Catalyst as the Reduction Reaction)

The 11-hydroxy-8-undecynal diethyl acetal (3) (83.23 g:0.322 mol), 210 g of n-hexane, 0.01 g of a 25% aqueous sodium hydroxide solution and 0.24 g of a Lindlar catalyst were placed in a stainless steel autoclave having an internal volume of 600 ml, subjected to addition of 0.5 MPa of hydrogen at a reaction solution temperature of 45 to 50° C., and then stirred for one hour. The reaction solution was filtered, and the filtrate was subjected to typical work-up of washing, drying and concentration to obtain the intended (Z)-11-hydroxy-8-undecenal diethyl acetal (8) (83.54 g:0.298 mol). The E:Z ratio of the product was 0:100 and the yield was 92.55%.

(Z)-11-Hydroxy-8-undecenal diethyl acetal (8)

IR (D-ATR): ν=3443, 3006, 2974, 2928, 2857, 1444, 1374, 1345, 1127, 1057, 875, 722 cm⁻¹.

¹H-NMR (500 MHz, CDCl₃): δ=1.18 (6H, t, J=7.1 Hz), 1.22-1.33 (8H, m), 1.56-1.60 (2H, m), 1.68 (1H, s), 2.03 (2H, q, J=6.9 Hz), 2.28-2.32 (2H, m), 3.44-3.50 (2H, m), 3.58-3.63 (4H, m), 4.46 (1H, t, J=5.8 Hz), 5.31-5.37 (1H, m), 5.49-5.55 (1H, m) ppm.

¹³C-NMR (125 MHz, CDCl₃): δ=15.29, 24.63, 27.24, 29.11, 29.26, 29.51, 30.75, 33.48, 60.75, 62.22, 102.85, 125.01, 133.24 ppm.

GC-MS (EI, 70 eV): 27, 41, 57, 75, 89, 103, 121, 135, 149, 167, 182, 197, 213, 227, 241, 257, 281 (M⁺).

Example 10

<Synthesis of (Z)-14-hydroxy-11-tetradecenal diethyl acetal (8)> (n=9, R¹=CH₂CH₃, R²=CH₂CH₃, and Hydrogenation Reaction with Lindlar Catalyst as the Reduction Reaction)

The 14-hydroxy-11-tetradecynal diethyl acetal (3) (90.00 g:0.265 mol), 100 g of n-hexane, 0.01 g of a 25% aqueous sodium hydroxide solution and 0.24 g of a Lindlar catalyst were placed in a stainless steel autoclave having an internal volume of 600 ml, subjected to addition of 0.5 MPa of hydrogen at a reaction solution temperature of 45 to 50° C., and then stirred for one hour. The reaction solution was filtered, and the filtrate was subjected to typical work-up of washing, drying and concentration to obtain the intended (Z)-14-hydroxy-11-tetradecenal diethyl acetal (8) (91.73 g:0.265 mol). The E:Z ratio of the product was 1:99 and the yield was 100%.

(Z)-14-Hydroxy-11-tetradecenal diethyl acetal (8)

Colorless to pale yellow oily liquid

IR (D-ATR): ν=3422, 2974, 2924, 2854, 1465, 1374, 1345, 1126, 1059, 998, 721 cm⁻¹.

¹H-NMR (500 MHz, CDCl₃): δ=1.19 (6H, t, J=7.1 Hz), 1.21-1.39 (14H, m), 1.56-1.61 (3H, m), 2.04 (2H, q, J=6.7 Hz), 2.29-2.33 (2H, m), 3.44-3.50 (2H, m), 3.59-3.65 (4H, m), 4.46 (1H, t, J=5.8 Hz), 5.32-5.37 (1H, m), 5.51-5.57 (1H, m) ppm.

¹³C-NMR (125 MHz, CDCl₃): δ=15.19, 24.69, 27.31, 29.20, 29.41, 29.44, 29.47, 29.62, 30.75, 33.52, 60.75, 62.25, 102.91, 124.92, 133.40 ppm.

GC-MS (EI, 70 eV): 29, 47, 75, 103, 119, 135, 153, 175, 191, 208, 224, 255, 283, 299 (M⁺).

Example 11

<Synthesis of (Z)-11-chloro-8-undecenal diethyl acetal (9)> (n=6, R¹=CH₂CH₃, R²=CH₂CH₃, X=Cl, Methanesulfonyl Chloride as the Halogenating Agent, and Pyridine as the Base)

In a nitrogen atmosphere, the (Z)-11-hydroxy-8-undecenal diethyl acetal (8) (81.18 g:0.290 mol), pyridine (34.38 g:0.435 mol) and N,N-dimethylformamide (330 g) were placed in a reactor, and stirred at a solution temperature of 0 to 5° C. for 20 minutes. The solution was subjected to dropwise addition of methanesulfonyl chloride (46.38 g:0.405 mol) at a solution temperature of 10° C. or less over 30 minutes, and then stirred at a reaction solution temperature of 20 to 25° C. for 2 hours and then at a reaction solution temperature of 55 to 60° C. for 6 hours. The reaction solution was cooled to 40° C. or less, subjected to addition of pure water (800 g) and n-hexane (500 g), and then stirred for 30 minutes. The organic phase separated was subjected to typical work-up of washing, drying and concentration to obtain the intended (Z)-11-chloro-8-undecenal diethyl acetal (9) (74.60 g:0.259 mol). The yield was 89.27%.

(Z)-11-Chloro-8-tetradecenal diethyl acetal (9)

Colorless to pale yellow oily liquid

IR (D-ATR): ν=3010, 2975, 2928, 2856, 1730, 1654, 1444, 1374, 1345, 1295, 1238, 1128, 1062, 1004, 738, 665 cm⁻¹.

¹H-NMR (500 MHz, CDCl₃): δ=1.19 (6H, t, J=7.1 Hz), 1.21-1.34 (8H, m), 1.57-1.61 (2H, m), 2.06 (2H, q, J=6.9 Hz), 2.48-2.52 (2H, m), 3.44-3.51 (4H, m), 3.59-3.65 (2H, m), 4.47 (1H, t, J=5.7 Hz), 5.33-5.38 (1H, m), 5.48-5.54 (1H, m) ppm.

¹³C-NMR (125 MHz, CDCl₃): δ=15.32, 24.65, 27.31, 29.13, 29.38, 30.65, 33.53, 44.21, 60.78, 102.88, 124.82, 133.17 ppm.

GC-MS (EI, 70 eV): 29, 47, 61, 75, 89, 103, 121, 142, 157, 184, 201, 215, 231, 247, 275 (M⁺).

Example 12

<Synthesis of (Z)-14-chloro-11-tetradecenal diethyl acetal (9)> (n=9, R¹=CH₂CH₃, R²=CH₂CH₃, X=Cl, Methanesulfonyl Chloride as the Halogenating Agent, and Pyridine as the Base)

In a nitrogen atmosphere, the (Z)-14-hydroxy-11-tetradecenal diethyl acetal (8) (70.00 g:0.204 mol), pyridine (24.22 g:0.306 mol) and N,N-dimethylformamide (280 g) were placed in a reactor, and stirred at a solution temperature of 0 to 5° C. for 15 minutes. The solution was subjected to dropwise addition of methanesulfonyl chloride (32.73 g:0.286 mol) at a solution temperature of 10° C. or less over one hour, and then stirred at a reaction solution temperature of 20 to 25° C. for 3 hours and then at a reaction solution temperature of 55 to 60° C. for 2 hours. The reaction solution was cooled to 40° C. or less, subjected to addition of pure water (1000 g), n-hexane (1000 g) and acetic acid (20 g), and then stirred for 30 minutes. The organic phase separated was subjected to typical work-up of washing, drying and concentration to obtain the intended (Z)-14-chloro-11-tetradecenal diethyl acetal (9) (60.46 g:0.165 mol). The yield was 80.84%.

(Z)-14-Chloro-11-tetradecenal diethyl acetal (9)

Colorless to pale yellow oily liquid
IR (D-ATR): ν=2974, 2925, 2854, 1728, 1656, 1457, 1445, 1373, 1345, 1294, 1239, 1127, 1062, 997, 722, 660 $cm^{-1}$.
$^1$H-NMR (500 MHz, CDCl$_3$): δ=1.19 (6H, t, J=7.1 Hz), 1.23-1.37 (14H, m), 1.56-1.63 (2H, m), 2.03 (2H, q, J=6.9 Hz), 2.48-2.53 (2H, m), 3.44-3.49 (4H, m), 3.59-3.69 (2H, m), 4.47 (1H, t, J=5.7 Hz), 5.33-5.39 (1H, m), 5.49-5.55 (1H, m) ppm.
$^{13}$C-NMR (125 MHz, CDCl$_3$): δ=15.33, 24.72, 27.36, 29.21, 29.44, 29.49, 29.51, 30.67, 33.56, 44.22, 60.77, 102.93, 124.75, 133.27 ppm.
GC-MS (EI, 70 eV): 25, 41, 57, 75, 103, 119, 135, 157, 176, 192, 215, 236, 255, 273, 317 (M$^+$).

Example 13

<Synthesis of (Z)-14-methanesulfonyloxy-11-tetradecenal diethyl acetal (9)> (n=9, R$^1$=CH$_2$CH$_3$, R$^2$=CH$_2$CH$_3$, X=OMs, Methanesulfonyl Chloride as the Alkylsulfonating Agent, and Triethylamine as the Base)

In a nitrogen atmosphere, the (Z)-14-hydroxy-11-tetradecenal diethyl acetal (8) (5.00 g:0.015 mol), triethylamine (2.22 g:0.022 mol) and dichloromethane (20 g) were placed in a reactor, and stirred at a solution temperature of 0 to 5° C. for 15 minutes. The solution was subjected to dropwise addition of methanesulfonyl chloride (1.84 g:0.016 mol) at a solution temperature of 10° C. or less over 5 minutes, and then stirred at a reaction solution temperature of 20 to 25° C. for 3 hours. The reaction solution was subjected to addition of pure water (50 g) and n-hexane (200 g), and then stirred for 30 minutes. The organic phase separated was subjected to typical work-up of washing, drying and concentration to obtain the intended (Z)-14-methanesulfonyloxy-11-tetradecenal diethyl acetal (9) (5.48 g). The (Z)-14-methanesulfonyloxy-11-tetradecenal diethyl acetal (9) cannot be detected precisely by GC analysis. Hence, the yield was calculated as the total yield of two steps after the next step of the elimination reaction.

(Z)-14-Methanesulfonyloxy-11-tetradecenal diethyl acetal (9)

Colorless or pale yellow oily liquid
IR (D-ATR): ν=$cm^{-1}$.
$^1$H-NMR (500 MHz, CDCl$_3$): δ=1.19 (6H, t, J=5.5 Hz), 1.26-1.36H (14H, m), 1.56-1.60 (2H, m), 2.02 (2H, q, J=7.4 Hz), 2.47-2.51 (2H, m), 2.99 (3H, s), 3.44-3.50 (2H, m), 3.59-3.65 (2H, m), 4.19 (2H, t, J=6.9 Hz), 4.46 (1H, t, J=5.6 Hz), 5.29-5.36 (1H, m), 5.52-5.57 (1H, m) ppm.
$^{13}$C-NMR (125 MHz, CDCl$_3$): δ=15.31, 24.69, 27.28, 27.32, 29.19, 29.41, 29.45, 29.48, 31.53, 33.54, 37.42, 60.77, 69.24, 102.91, 122.52, 134.18 ppm.

Example 14

<Synthesis of (Z)-8,10-undecadienal diethyl acetal (10)> (n=6, R$^1$=CH$_2$CH$_3$, R$^2$=CH$_2$CH$_3$, and Potassium t-butoxide as the Base)

In a nitrogen atmosphere, potassium t-butoxide (10.12 g:0.090 mol) and tetrahydrofuran (80 g) were placed in a reactor, and stirred at a solution temperature of 0 to 5° C. for 15 minutes. The solution was subjected to dropwise addition of the (Z)-11-chloro-8-undecenal diethyl acetal (9) (20.00 g:0.069 mol) at a solution temperature of 10° C. or less over 30 minutes, and then stirred at room temperature for 4 hours. The reaction solution was subjected to addition of pure water (100 g) and n-hexane (100 g), and then stirred for 30 minutes. The organic phase separated was subjected to typical work-up of washing, drying and concentration to obtain the intended (Z)-8,10-undecadienal diethyl acetal (10) (17.52 g:0.069 mol). The yield was 100%.

(Z)-8,10-Undecadienal diethyl acetal (10)

Colorless to pale yellow oily liquid
IR (D-ATR): ν=3085, 2975, 2928, 2856, 1654, 1592, 1457, 1443, 1374, 1344, 1128, 1063, 997, 902, 787, 728, 655, 618, 612 $cm^{-1}$.
$^1$H-NMR (500 MHz, CDCl$_3$): δ=1.19 (6H, t, J=7.1 Hz), 1.22-1.42 (8H, m), 1.57-1.61 (2H, m), 2.17 (2H, dq, J=1.4, 7.4 Hz), 3.45-3.51 (2H, m), 3.60-3.65 (2H, m), 4.46 (1H, t, J=6.0 Hz), 5.07 (1H, d, J=10.3 Hz), 5.16 (1H, dd, J=1.9 Hz, 15.8 Hz), 5.44 (1H, dt, J=8.4, 8.9 Hz), 5.98 (1H, t, J=10.9 Hz), 6.61 (1H, ddt, J=1.1, 10.6, 17.4) ppm.
$^{13}$C-NMR (125 MHz, CDCl$_3$): δ=15.32, 24.65, 27.64, 29.08, 29.28, 29.45, 33.44, 33.56, 60.77, 102.88, 116.67, 129.12, 132.27, 132.90 ppm.
GC-MS (EI, 70 eV): 29, 47, 59, 75, 91, 103, 121, 135, 150, 165, 179, 195, 211, 225, 240 (M$^+$).

Example 15

<Synthesis of (Z)-11,13-tetradecadienal diethyl acetal (10)> (n=9, R$^1$=CH$_2$CH$_3$, R$^2$=CH$_2$CH$_3$, and Potassium t-butoxide as the Base)

In a nitrogen atmosphere, potassium t-butoxide (17.36 g:0.155 mol) and tetrahydrofuran (200 g) were placed in a reactor, and stirred at a solution temperature of from 0 to 5° C. for 15 minutes. The solution was subjected to dropwise addition of the (Z)-14-chloro-11-tetradecenal diethyl acetal (9) (48.00 g:0.119 mol) at a solution temperature of 10° C. or less over 30 minutes, and then stirred at room temperature for 5 hours. The reaction mixture was subjected to addition of pure water (200 g) and n-hexane (200 g), and then stirred for 30 minutes. The organic phase separated was subjected to typical work-up of washing, drying and concentration to obtain the intended (Z)-11,13-tetradecadienal diethyl acetal (10) (43.97 g:0.119 mol). The yield was 100%.

Example 16

<Synthesis of (Z)-11,13-tetradecadienal diethyl acetal (10)> (n=9, R$^1$=CH$_2$CH$_3$, R$^2$=CH$_2$CH$_3$, (Z)-14-methanesulfonyloxy-11-tetradecenal diethyl acetal (9) as the Substrate, and Potassium t-butoxide as the Base)

In a nitrogen atmosphere, potassium t-butoxide (0.88 g:0.008 mol) and tetrahydrofuran (10 g) were placed in a reactor, and stirred at a solution temperature of from 0 to 5° C. for 30 minutes. The solution was subjected to dropwise addition of the (Z)-14-methanesulfonyloxy-11-tetradecenal diethyl acetal (9) (2.00 g) at a solution temperature of 10° C. or less over 10 minutes, and then stirred at room temperature for 2 hours. The reaction mixture was subjected to addition of pure water (10 g) and n-hexane (20 g), and then stirred for 30 minutes. The organic phase separated was subjected to typical work-up of washing, drying and concentration to obtain the intended (Z)-11,13-tetradecadienal diethyl acetal (10) (1.15 g:0.003 mol). The total yield of the two steps from the (Z)-14-hydroxy-11-tetradecenal diethyl acetal (8) was 50.0%.

(Z)-11,13-Tetradecadienal diethyl acetal (10)

Colorless to pale yellow oily liquid
IR (D-ATR): v=3086, 2974, 2925, 2854, 1644, 1458, 1444, 1373, 1345, 1127, 1061, 997, 902, 786, 721, 656, 612 cm$^{-1}$.
$^1$H-NMR (500 MHz, CDCl$_3$): δ=1.19 (6H, t, J=7.1 Hz), 1.23-1.38 (14H, m), 1.57-1.61 (2H, m), 2.17 (2H, dt, J=1.1, 7.4 Hz), 3.44-3.51 (2H, m), 3.60-3.65 (2H, m), 4.47 (1H, t, J=5.8 Hz), 5.07 (1H, d, J=10.3 Hz), 5.16 (1H, dd, J=2.1 Hz, 17 Hz), 5.44 (1H, dt, J=8.1, 9.9 Hz), 5.97 (1H, t, J=10.9 Hz), 6.63 (1H, ddt, J=1.2, 11.1, 17.4) ppm.
$^{13}$C-NMR (125 MHz, CDCl$_3$): δ=15.33, 24.73, 27.70, 29.17, 29.42, 29.44, 29.47, 29.51, 29.57, 33.56, 60.76, 102.93, 116.61, 129.06, 132.30, 133.03 ppm.
GC-MS (EI, 70 eV): 29, 47, 61, 75, 89, 103, 121, 135, 149, 163, 177, 192, 207, 221, 236, 253, 267, 282 (M$^+$).

Example 17

<Synthesis of (Z)-8,10-undecadienal (11)> (n=6 and Oxalic Acid as the Acid)

In a nitrogen atmosphere, the (Z)-8,10-undecadienal diethyl acetal (10) (15.97 g:0.065 mol), tetrahydrofuran (160 g), pure water (160 g) and oxalic acid dihydrate (16.75 g:0.132 mol) were placed in a reactor, and refluxed with stirring for 5 hours. The reaction solution was cooled to 40° C. or less, subjected to addition of sodium chloride (20 g) and n-hexane (300 g), and then stirred for 30 minutes. The organic phase separated was subjected to typical work-up of washing, drying and concentration to obtain 11.75 g of a crude product. The crude product was distilled under reduced pressure to obtain the intended (Z)-8,10-undecadienal (11) (9.94 g:0.056 mol). The E:Z ratio of the product was 1:99 and the yield was 86.15%.

(Z)-8,10-Undecadienal (11)

IR (D-ATR): v=3084, 3007, 2930, 2856, 2718, 1725, 1643, 1592, 1463, 1434, 999, 904, 785, 727, 657 cm$^{-1}$.
$^1$H-NMR (500 MHz, CDCl$_3$): δ=1.24-1.43 (6H, m), 1.59-1.67 (2H, m), 2.17 (2H, dq, J=1.4, 7.4 Hz), 2.41 (2H, dt, J=1.9, 7.3 Hz), 5.07 (1H, d, J=10.3 Hz), 5.17 (1H, dd, J=1.9, 17.2 Hz), 5.44 (1H, dt, J=8.0, 10.0 Hz), 5.99 (1H, t, J=10.7 Hz), 6.63 (1H, ddt, J=1.2, 10.5, 17.9 Hz), 9.75 (1H, t, J=1.9 Hz) ppm.
$^{13}$C-NMR (125 MHz, CDCl$_3$): δ=21.94, 27.52, 28.81, 28.92, 29.26, 43.80, 116.79, 129.24, 132.17, 132.63, 202.77 ppm.
GC-MS (EI, 70 eV): 29, 41, 54, 67, 79, 98, 109, 123, 137, 151, 166 (M$^+$).

Example 18

<Synthesis of (Z)-11,13-tetradecadienal (11)> (n=9 and Oxalic Acid as the Acid)

In a nitrogen atmosphere, the (Z)-11,13-tetradecadienal diethyl acetal (10) (42.00 g:0.114 mol), tetrahydrofuran (420 g), pure water (420 g) and oxalic acid dihydrate (14.32 g:0.114 mol) were placed in a reactor, and refluxed with stirring for 5 hours. The reaction solution was cooled to 40° C. or less, subjected to addition of sodium chloride (42 g), and then stirred for 30 minutes. The organic phase separated was subjected to typical work-up of washing, drying and concentration to obtain 33.58 g of a crude product. The crude product was distilled under reduced pressure to obtain the intended (Z)-11,13-tetradecadienal (11) (29.55 g:0.101 mol). The E:Z ratio of the product was 1:99 and the yield was 88.60%.

(Z)-11,13-Tetradecadienal (11)

IR (D-ATR): v=3084, 3008, 2925, 2854, 2714, 1727, 1643, 1593, 1464, 1369, 1123, 1067, 997, 902, 785, 722, 652 cm$^{-1}$.
$^1$H-NMR (500 MHz, CDCl$_3$): δ=1.25-1.42 (12H, m), 1.58-1.64 (2H, m), 2.14-2.19 (2H, m), 2.41 (2H, dt, J=1.7, 7.8 Hz), 5.07 (1H, d, J=10.0 Hz), 5.16 (1H, d, J=16.8 Hz), 5.44 (1H, dt, J=7.7, 10.3 Hz), 5.98 (1H, t, J=10.9 Hz), 6.63 (1H, ddt, J=1.0, 10.6, 16.8), 9.75 (1H, t, J=1.9 Hz) ppm.
$^{13}$C-NMR (125 MHz, CDCl$_3$): δ=22.02, 27.66, 29.10, 29.12, 29.27, 29.31, 29.35, 29.53, 43.86, 116.65, 129.09, 132.28, 132.96, 202.89 ppm.
GC-MS (EI, 70 eV): 29, 41, 54, 67, 81, 95, 109, 121, 135, 151, 165, 179, 193, 208 (M$^+$).

The invention claimed is:
1. A method for producing an (E)-dienal compound, comprising the steps of:
metalizing a terminal alkyne of an alkynal acetal compound represented by formula (1):

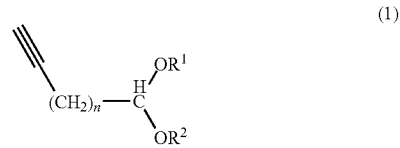

wherein n is an integer of from 2 to 11, and R$^1$ and R$^2$ each independently represents a monovalent hydrocarbon group having from 1 to 10 carbon atoms, or R$^1$ and R$^2$ are coupled together to form a divalent hydrocarbon group having from 2 to 10 carbon atoms, through a metalation reaction of the alkynal acetal compound to obtain an organic metal compound represented by formula (2):

(2)

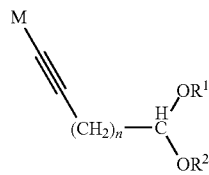

wherein M represents a cationic moiety;
reacting the organic metal compound with ethylene oxide through an addition reaction to obtain a hydroxyalkynal acetal compound represented by formula (3):

(3)

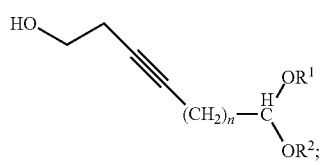

reducing the hydroxyalkynal acetal compound through a reduction reaction of converting a triple bond of the hydroxyalkynal acetal compound into an (E)-double bond to obtain an (E)-hydroxyalkenal acetal compound represented by formula (4):

(4)

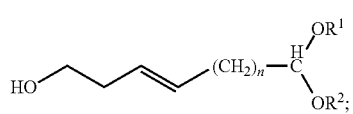

converting a hydroxyl group of the (E)-hydroxyalkenal acetal compound into a leaving group X through a functional group conversion reaction of the (E)-hydroxyalkenal acetal compound to obtain an (E)-alkenal acetal compound having the leaving group X represented by formula (5):

(5)

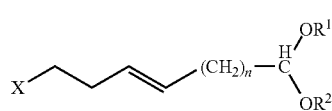

wherein X represents a leaving group;
eliminating HX from the (E)-alkenal acetal compound having the leaving group X through an elimination reaction of the (E)-alkenal acetal compound to obtain an (E)-dienal acetal compound represented by formula (6):

(6)

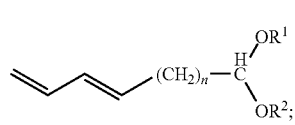

and
hydrolyzing the (E)-dienal acetal compound through a hydrolysis reaction of converting an acetal of the (E)-dienal acetal compound into an aldehyde to obtain the (E)-dienal compound represented by formula (7):

(7)

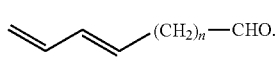

2. The method for producing an (E)-dienal compound according to claim 1, wherein the (E)-dienal compound is (E)-11,13-tetradecadienal.

3. A method for producing a (Z)-dienal compound, comprising the steps of: metalizing a terminal alkyne of an alkynal acetal compound represented by formula (1):

(1)

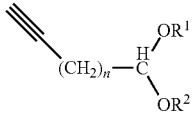

wherein n is an integer of from 2 to 11, and $R^1$ and $R^2$ each independently represents a monovalent hydrocarbon group having from 1 to 10 carbon atoms, or $R^1$ and $R^2$ are coupled together to form a divalent hydrocarbon group having from 2 to 10 carbon atoms, through a metalation reaction of the alkynal acetal compound to obtain an organic metal compound represented by formula (2):

(2)

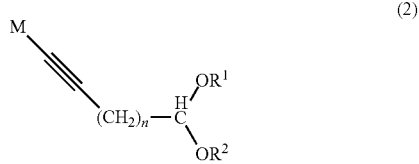

wherein M represents a cationic moiety;
reacting the organic metal compound with ethylene oxide through an addition reaction to obtain a hydroxyalkynal acetal compound represented by formula (3):

(3)

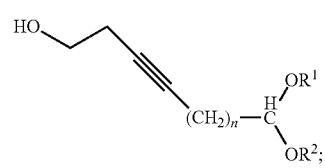

reducing the hydroxyalkynal acetal compound through a reduction reaction of converting a triple bond of the hydroxyalkynal acetal compound into a (Z)-double bond to obtain a (Z)-hydroxyalkenal acetal compound represented by formula (8):

(8)

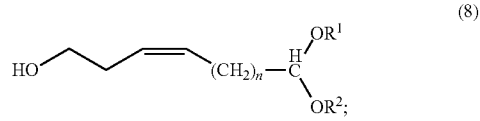

converting a hydroxyl group of the (Z)-hydroxyalkenal acetal compound into a leaving group X through a functional group conversion reaction of the (Z)-hydroxyalkenal acetal compound to obtain a (Z)-alkenal acetal compound having the leaving group X represented by formula (9):

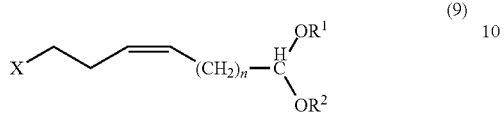
(9)

wherein X represents a leaving group;

eliminating HX from the (Z)-alkenal acetal compound having the leaving group X through an elimination reaction of the (Z)-alkenal acetal compound to obtain a (Z)-dienal acetal compound represented by formula (10):

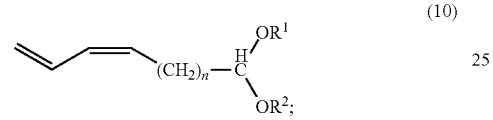
(10)

and hydrolyzing the (Z)-dienal acetal compound through a hydrolysis reaction of converting an acetal of the (Z)-dienal acetal compound into an aldehyde to obtain the (Z)-dienal compound represented by formula (11):

(11)

4. The method for producing a (Z)-dienal compound according to claim 3, wherein the (Z)-dienal compound is (Z)-11,13-tetradecadienal.

5. A hydroxyalkynal acetal compound represented by formula (3):

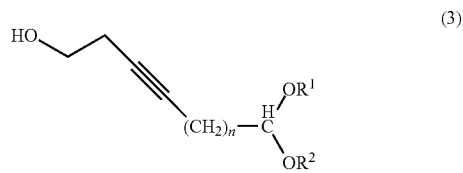
(3)

wherein n is an integer of from 2 to 11, and $R^1$ and $R^2$ each independently represents a monovalent hydrocarbon group having from 1 to 10 carbon atoms.

6. An (E)-hydroxyalkenal acetal compound represented by formula (4):

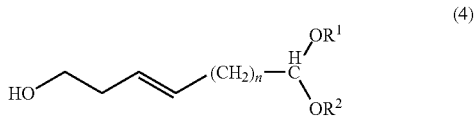
(4)

wherein n is an integer of from 2 to 11, and $R^1$ and $R^2$ each independently represents a monovalent hydrocarbon group having from 1 to 10 carbon atoms.

7. A (Z)-hydroxyalkenal acetal compound represented by formula (8m):

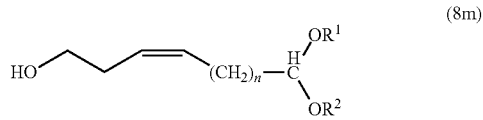
(8m)

wherein m is an integer of from 5 to 11, and $R^1$ and $R^2$ each independently represents a monovalent hydrocarbon group having from 1 to 10 carbon atoms.

* * * * *